United States Patent
Tsujimoto et al.

(10) Patent No.: US 6,461,852 B1
(45) Date of Patent: Oct. 8, 2002

(54) **DIHYDRODIPICOLINATE SYNTHASE FROM *BACILLUS METHANOLICUS***

(75) Inventors: Nobuharu Tsujimoto; Hisashi Yasueda; Yoshio Kawahara; Shinichi Sugimoto, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/631,828

(22) Filed: Aug. 3, 2000

(30) Foreign Application Priority Data

Aug. 4, 1999 (JP) .......................................... 11-221468

(51) Int. Cl.[7] ................................................ C12N 9/88
(52) U.S. Cl. ...................................................... 435/232
(58) Field of Search ........................... 435/232; 530/350

(56) References Cited

U.S. PATENT DOCUMENTS

| | | | |
|---|---|---|---|
| 4,346,170 A | 8/1982 | Sano et al. ................. | 435/115 |
| 5,426,052 A | 6/1995 | Flickinger et al. | |

FOREIGN PATENT DOCUMENTS

| | | |
|---|---|---|
| EP | 0 841 395 | 5/1998 |
| KR | 92-8382 | 9/1992 |
| WO | WO 96/40934 | 12/1996 |
| WO | WO 99/20783 | 4/1999 |

OTHER PUBLICATIONS

GenBank Accession No. E46665. dihydrodipicolinate synthase (EC 4.2.1.52) dapA [similarity]—*Bacillus subtilis*. Created May 3, 1994.*

L. Eggeling, et al., Applied Microbiology and Biotechnology, vol. 49, No. 1, pp. 24–30, "Improved L–Lysine Yield With Corynebacterium Glutamicum: Use of DAPA Resulting in Increased Flux Combined With Growth Limitation", 1998.

D. A. Mills, et al., Applied and Environmental Microbiology, vol. 59, No. 9, pp. 2927–2937, "Cloning and Sequence Analysis of the MESO–Diaminopimelate Decarboxylase Gene From *Bacillus Methanolicus* MGA3 and Comparison to Other Decarboxylase Genes", Sep. 1993.

F. J. Shendel, et al., Applied and Environmental Microbiology, vol. 58, No. 9, pp. 2806–2814, "Cloning and Nucleotide Sequence of Gene Coding For Aspartokinase II From a Thermophilic *Methylotrophic Bacillus SP*", Sep. 1992.

G. H. Lee, et al., Biotechnology and Bioengineering, vol. 49, pp. 639–653, "Lysine Production From Methanol at 50°C Using *Bacillus Methanolicus*: Modeling Volume Control, Lysine Concentration, and Productivity Using a Three–Phase Continuous Simulation", Oct. 4, 1996.

N.Y. Chen, et al., Database SWAL 'Online', AC Q04796, pp. 1–2, "Dihydrodipicolinate Synthase (EC 4.2.1.52) (DHDPS) (Vegetative Protein 81)", Oct. 1, 1993.

A.V. Sorokin, et al., Database SWALL [Online], AC P42976, 1 page, "Dihydrodipocolinate Reductase (EC 1.3.1.26) (DHPR)", Nov. 1, 1995.

J. Bouvier, et al., The Journal of Biological Chemistry, vol. 259, NO. 23, pp. 14829–14834, "Nucleotide Sequence and Expression of the *Escherichia Coli* DAPB Gene", Dec. 10, 1984.

B. Dauce–Le Reverend, et al., European Journal of Applied Microbiology and Biotechnology, vol. 15, pp.227–231, "Improvement of *Escherichia Coli* Strains Overproducing Lysine Using Recombinant DNA Techiques", 1982.

A. Pisabarro, et al., Journal of Bacteriology, vol. 175, No. 9, pp. 2743–2749, "A Cluster of Three Genes (dapA,orf2, and dapB) of Brevibacterium Lactofermentum encodes Dihydrodipicolinate Synthase, Dihydrodipicolinate Reductase, and a Third Polypeptide of Unknown Function", May 1993

* cited by examiner

*Primary Examiner*—Ponnathapu Achutamurthy
*Assistant Examiner*—Kathleen M Kerr
(74) *Attorney, Agent, or Firm*—Oblon, Spivak, McClelland, Maier & Neustadt, P.C.

(57) ABSTRACT

The present invention provides dihydropicolinate synthase and dihydrodipicolinate reductase enzymes from *Bacillus methanolicus*, polynucleotides encoding the enzymes, and methods of producing L-lysinse in microorganisms expressing the enzymes.

4 Claims, No Drawings

SEQUENCE LISTING

```
<160> NUMBER OF SEQ ID NOS: 4

<210> SEQ ID NO 1
<211> LENGTH: 873
<212> TYPE: DNA
<213> ORGANISM: Bacillus methanolicus
<220> FEATURE:
<221> NAME/KEY: CDS
<222> LOCATION: (1)..(870)

<400> SEQUENCE: 1 atg gtt tct ttt ggt cga ata tca aca gct atg gtt aca cca ttt gat      48
Met Val Ser Phe Gly Arg Ile Ser Thr Ala Met Val Thr Pro Phe Asp
1               5                  10                  15 aac aaa ggt cat att gat ttt gca aaa aca acg caa ctc gtg aat cat      96
Asn Lys Gly His Ile Asp Phe Ala Lys Thr Thr Gln Leu Val Asn His
                20                  25                  30 tta att aat aat ggt tca gat tct tta gtt gtt gtc ggt act act gga     144
Leu Ile Asn Asn Gly Ser Asp Ser Leu Val Val Val Gly Thr Thr Gly
            35                  40                  45 gag tca gcc aca ctt aca aaa gaa gaa aaa ttg gcg ctt ttt cag cat     192
Glu Ser Ala Thr Leu Thr Lys Glu Glu Lys Leu Ala Leu Phe Gln His
50                  55                  60 gta gta aaa gta gtt gaa aaa aga gtc cct gtt att gca ggc acc gga     240
Val Val Lys Val Val Glu Lys Arg Val Pro Val Ile Ala Gly Thr Gly
65                  70                  75                  80 agc aat aat act tat gat tca atc gaa atg aca aaa aaa gca gaa aaa     288
Ser Asn Asn Thr Tyr Asp Ser Ile Glu Met Thr Lys Lys Ala Glu Lys
                85                  90                  95 atg ggc gtc gat gcg att ttg gca gtt gct ccg tat tat aac aaa cca     336
Met Gly Val Asp Ala Ile Leu Ala Val Ala Pro Tyr Tyr Asn Lys Pro
            100                 105                 110 aac cag gaa gga tta tat caa cat ttt aag gca att gct gaa agt aca     384
Asn Gln Glu Gly Leu Tyr Gln His Phe Lys Ala Ile Ala Glu Ser Thr
        115                 120                 125 tcc ctt cct gtt atc att tat aac att ccc gga aga tct gtt gtg aat     432
Ser Leu Pro Val Ile Ile Tyr Asn Ile Pro Gly Arg Ser Val Val Asn
    130                 135                 140 atc gag cct gaa acg gtc atc cgt ttg tcc aag att ccg aac att gtt     480
Ile Glu Pro Glu Thr Val Ile Arg Leu Ser Lys Ile Pro Asn Ile Val
145                 150                 155                 160 ggt atc aaa gaa gca ggc ggg aat ctt agt gcg atg acg caa att att     528
Gly Ile Lys Glu Ala Gly Gly Asn Leu Ser Ala Met Thr Gln Ile Ile
                165                 170                 175 gcc aat aca gat gac gat ttt ctt ttg tat agc gga gac gac ggt tta     576
```

```
                                                              -continued

Ala Asn Thr Asp Asp Phe Leu Leu Tyr Ser Gly Asp Asp Gly Leu
            180                 185                 190 acc ttg cca gta ctg tcc att ggc gga acc ggg gtt att tct gtg gca    624
Thr Leu Pro Val Leu Ser Ile Gly Gly Thr Gly Val Ile Ser Val Ala
        195                 200                 205 tcc cat gtt atc gga aat gaa atg caa gaa atg atc agt gca ttt tta    672
Ser His Val Ile Gly Asn Glu Met Gln Glu Met Ile Ser Ala Phe Leu
            210                 215                 220 aat gga gat tat gaa cgt gcg gca aaa att cat caa aag ctg ctt ccg    720
Asn Gly Asp Tyr Glu Arg Ala Ala Lys Ile His Gln Lys Leu Leu Pro
225                 230                 235                 240 ctt atg gat gga tta ttt atc gct cca aac cct gta ccg gtt aaa act    768
Leu Met Asp Gly Leu Phe Ile Ala Pro Asn Pro Val Pro Val Lys Thr
                245                 250                 255 gct ttg caa att aaa ggc atg gat gtc ggt tcg gtt cgc ttg cct ctt    816
Ala Leu Gln Ile Lys Gly Met Asp Val Gly Ser Val Arg Leu Pro Leu
            260                 265                 270 gtt ccg ctt act gaa caa gag cga aat aca gtg gca gca tta tta aat    864
Val Pro Leu Thr Glu Gln Glu Arg Asn Thr Val Ala Ala Leu Leu Asn
        275                 280                 285 gct tta taa                                                         873
Ala Leu
    290

<210> SEQ ID NO 2
<211> LENGTH: 290
<212> TYPE: PRT
<213> ORGANISM: Bacillus methanolicus

<400> SEQUENCE: 2

Met Val Ser Phe Gly Arg Ile Ser Thr Ala Met Val Thr Pro Phe Asp
1               5                   10                  15

Asn Lys Gly His Ile Asp Phe Ala Lys Thr Thr Gln Leu Val Asn His
                20                  25                  30

Leu Ile Asn Asn Gly Ser Asp Ser Leu Val Val Gly Thr Thr Gly
            35                  40                  45

Glu Ser Ala Thr Leu Thr Lys Glu Glu Lys Leu Ala Leu Phe Gln His
        50                  55                  60

Val Val Lys Val Val Glu Lys Arg Val Pro Val Ile Ala Gly Thr Gly
65                  70                  75                  80

Ser Asn Asn Thr Tyr Asp Ser Ile Glu Met Thr Lys Lys Ala Glu Lys
                85                  90                  95

Met Gly Val Asp Ala Ile Leu Ala Val Ala Pro Tyr Tyr Asn Lys Pro
            100                 105                 110

Asn Gln Glu Gly Leu Tyr Gln His Phe Lys Ala Ile Ala Glu Ser Thr
        115                 120                 125

Ser Leu Pro Val Ile Ile Tyr Asn Ile Pro Gly Arg Ser Val Val Asn
    130                 135                 140

Ile Glu Pro Glu Thr Val Ile Arg Leu Ser Lys Ile Pro Asn Ile Val
145                 150                 155                 160

Gly Ile Lys Glu Ala Gly Gly Asn Leu Ser Ala Met Thr Gln Ile Ile
                165                 170                 175

Ala Asn Thr Asp Asp Phe Leu Leu Tyr Ser Gly Asp Asp Gly Leu
            180                 185                 190

Thr Leu Pro Val Leu Ser Ile Gly Gly Thr Gly Val Ile Ser Val Ala
        195                 200                 205

Ser His Val Ile Gly Asn Glu Met Gln Glu Met Ile Ser Ala Phe Leu
```

-continued

```
            210                 215                 220
Asn Gly Asp Tyr Glu Arg Ala Ala Lys Ile His Gln Lys Leu Leu Pro
225                     230                 235                 240

Leu Met Asp Gly Leu Phe Ile Ala Pro Asn Pro Val Pro Val Lys Thr
                    245                 250                 255

Ala Leu Gln Ile Lys Gly Met Asp Val Gly Ser Val Arg Leu Pro Leu
                260                 265                 270

Val Pro Leu Thr Glu Gln Glu Arg Asn Thr Val Ala Ala Leu Leu Asn
            275                 280                 285

Ala Leu
    290

<210> SEQ ID NO 3
<211> LENGTH: 801
<212> TYPE: DNA
<213> ORGANISM: Bacillus methanolicus
<220> FEATURE:
<221> NAME/KEY: CDS
<222> LOCATION: (1)..(798)

<400> SEQUENCE: 3 atg gaa att gta aaa att gtt gta gca ggc ccg cgc gga cga atg ggg      48
Met Glu Ile Val Lys Ile Val Val Ala Gly Pro Arg Gly Arg Met Gly
1               5                   10                  15 cgg gaa gca gtc cat ctt gtc ggg aga aca gaa aat ttc gag ttg gca     96
Arg Glu Ala Val His Leu Val Gly Arg Thr Glu Asn Phe Glu Leu Ala
                20                  25                  30 gca gtg ctg gat aat aag aat gac gga aaa aat ctt tcc gaa ttg gaa    144
Ala Val Leu Asp Asn Lys Asn Asp Gly Lys Asn Leu Ser Glu Leu Glu
            35                  40                  45 ggt ttt caa gga ttt gat gcc cct gtg tat aca aat att gaa aaa tgt    192
Gly Phe Gln Gly Phe Asp Ala Pro Val Tyr Thr Asn Ile Glu Lys Cys
        50                  55                  60 ttt caa gat acc ggc gca gat gtc tta atc gat ttg acg act cct gaa    240
Phe Gln Asp Thr Gly Ala Asp Val Leu Ile Asp Leu Thr Thr Pro Glu
65                  70                  75                  80 gta ggc tac tat cat aca aaa acg gct ctc gaa tat gga gtg cgg cct    288
Val Gly Tyr Tyr His Thr Lys Thr Ala Leu Glu Tyr Gly Val Arg Pro
                85                  90                  95 gta gtt ggg acg acg ggt ttt acg aaa gat caa tta aaa gaa att gaa    336
Val Val Gly Thr Thr Gly Phe Thr Lys Asp Gln Leu Lys Glu Ile Glu
                100                 105                 110 gaa att tgc gaa gaa aag aaa ctt ggc tgc att ata gcg cca aat ttt    384
Glu Ile Cys Glu Glu Lys Lys Leu Gly Cys Ile Ile Ala Pro Asn Phe
            115                 120                 125 gcg gtt ggg gct gta tta atg atg aaa ttt tca caa atg gca gcc aag    432
Ala Val Gly Ala Val Leu Met Met Lys Phe Ser Gln Met Ala Ala Lys
        130                 135                 140 tat ttt caa gat att gaa att att gaa ctg cat cat gat caa aaa ttg    480
Tyr Phe Gln Asp Ile Glu Ile Ile Glu Leu His His Asp Gln Lys Leu
145                 150                 155                 160 gat gca ccg tcc gga aca gct gtc aaa aca gct gag atg att gcg gaa    528
Asp Ala Pro Ser Gly Thr Ala Val Lys Thr Ala Glu Met Ile Ala Glu
                165                 170                 175 gtg aga gaa gca aag aag cag ggt cat cca aat gaa aaa gaa acg atc    576
Val Arg Glu Ala Lys Lys Gln Gly His Pro Asn Glu Lys Glu Thr Ile
                180                 185                 190 atc ggt gca agg ggt gcg gat tat gaa gga atg cat att cat tct gtt    624
Ile Gly Ala Arg Gly Ala Asp Tyr Glu Gly Met His Ile His Ser Val
            195                 200                 205
```

```
cgt ttg ccg gga tta att gcc cat cag cag gtg atg ttt gga tca gac       672
Arg Leu Pro Gly Leu Ile Ala His Gln Gln Val Met Phe Gly Ser Asp
    210                 215                 220 ggg caa aca ttg acg atc cgc cac gat tcg tat aac cgg gca tct ttc       720
Gly Gln Thr Leu Thr Ile Arg His Asp Ser Tyr Asn Arg Ala Ser Phe
225                 230                 235                 240 atg tct ggc gta aag cat gcc gtt gag acg gtt tta aaa att gat acg       768
Met Ser Gly Val Lys His Ala Val Glu Thr Val Leu Lys Ile Asp Thr
                245                 250                 255 ttt gtt tac gga tta gaa aat att att gaa tag                           801
Phe Val Tyr Gly Leu Glu Asn Ile Ile Glu
            260                 265

<210> SEQ ID NO 4
<211> LENGTH: 266
<212> TYPE: PRT
<213> ORGANISM: Bacillus methanolicus

<400> SEQUENCE: 4

Met Glu Ile Val Lys Ile Val Ala Gly Pro Arg Gly Arg Met Gly
 1               5                  10                  15

Arg Glu Ala Val His Leu Val Gly Arg Thr Glu Asn Phe Glu Leu Ala
                20                  25                  30
Ala Val Leu Asp Asn Lys Asn Asp Gly Lys Asn Leu Ser Glu Leu Glu
            35                  40                  45
Gly Phe Gln Gly Phe Asp Ala Pro Val Tyr Thr Asn Ile Glu Lys Cys
50                  55                  60

Phe Gln Asp Thr Gly Ala Asp Val Leu Ile Asp Leu Thr Thr Pro Glu
65                  70                  75                  80
Val Gly Tyr Tyr His Thr Lys Thr Ala Leu Glu Tyr Gly Val Arg Pro
                85                  90                  95
Val Val Gly Thr Thr Gly Phe Thr Lys Asp Gln Leu Lys Glu Ile Glu
                100                 105                 110

Glu Ile Cys Glu Glu Lys Lys Leu Gly Cys Ile Ile Ala Pro Asn Phe
            115                 120                 125
Ala Val Gly Ala Val Leu Met Met Lys Phe Ser Gln Met Ala Ala Lys
            130                 135                 140
Tyr Phe Gln Asp Ile Glu Ile Ile Glu Leu His His Asp Gln Lys Leu
145                 150                 155                 160

Asp Ala Pro Ser Gly Thr Ala Val Lys Thr Ala Glu Met Ile Ala Glu
                165                 170                 175
Val Arg Glu Ala Lys Lys Gln Gly His Pro Asn Glu Lys Glu Thr Ile
                180                 185                 190

Ile Gly Ala Arg Gly Ala Asp Tyr Glu Gly Met His Ile His Ser Val
            195                 200                 205

Arg Leu Pro Gly Leu Ile Ala His Gln Gln Val Met Phe Gly Ser Asp
            210                 215                 220
Gly Gln Thr Leu Thr Ile Arg His Asp Ser Tyr Asn Arg Ala Ser Phe
225                 230                 235                 240
Met Ser Gly Val Lys His Ala Val Glu Thr Val Leu Lys Ile Asp Thr
                245                 250                 255

Phe Val Tyr Gly Leu Glu Asn Ile Ile Glu
            260                 265
```

DIHYDRODIPICOLINATE SYNTHASE FROM *BACILLUS METHANOLICUS*

BACKGROUND OF THE INVENTION

1. Field of the Invention

The present invention relates to dihydrodipicolinate synthase and dihydrodipicolinate reductase derived thermophilic Bacillus bacteria and genes coding for them.

2. Related Art

In the production of L-lysine by fermentation, strains isolated from nature or artificial mutants thereof have been used in order to improve the productivity. Many artificial mutant strains that produce L-lysine are known, and many of them are aminoethylcysteine (AEC) resistant strains and belong to the genus Brevibacterium, Corynebacterium, Bacillus or Escherichia. Further, various techniques have been disclosed for increasing the amino acid production, for example, use of a transformant obtained by using recombinant DNA (U.S. Pat. No. 4,278,765).

Dihydrodipicolinate synthase (abbreviated as "DDPS" hereinafter) is an enzyme that synthesizes dihydrodipicolinate through dehydration condensation of aspartic acid semialdehyde and pyruvic acid, and this reaction serves as an entrance of the branching into the L-lysine biosynthesis system in the biosynthesis of amino acids of aspartic acid type. Further, dihydrodipicolinate reductase (abbreviated as "DDPR" hereinafter) is known as one of important enzymes of the L-lysine biosynthesis system, which catalyzes the reaction in which the dihydrodipicoliniate generated in the aforementioned reaction is reduced to generate piperidinedicarboxylic acid.

As for microorganisms belonging to the genus Escherichia or Corynebacterium, the gene (dapA) which codes for DDPS has been cloned, and the nucleotide sequence thereof has also be determined. As for the genus Escherichia, methods for producing L-lysine by enhancing DDPS have been disclosed in Japanese Patent Laid-open Publication (Kokai) No. 56-18596/1981, U.S. Pat. No. 4,346,170 and Applied Microbiology and Biotechnology, 15, pp.227–331 (1982). Furthermore, a method for producing L-lysine using an Escherichia bacterium introduced with DDPS derived form Corynebacterium bacteria, which is known not to suffer feedback inhibition by L-lysine, has been disclosed in Korean Patent Publication No. 92–8382.

The gene coding for DDPR (dapB) has also been already obtained from the genus Escherichia (Bouvier, J. et al., *J. Biol. Chem.*, 259, 14829 (1984)) and the genus Corynebacterium (*Journal of Bacteriology*, 175 (9), 2743– 2749 (1993)). Furthermore, there has also been disclosed a method for improving production rate and productivity of L-lysine by enhancing the dapB gene derived from Corynebacterium bacterium together with the aspartokinase gene (WO96/40934).

The current mainstream of the L-lysine production is the fermentative production by using a coryneform bacterium or an Escherichia bacterium. In this production, however, enzymes required for the fermentation may be inactivated or the production bacteria may be killed due to temperature increase in the medium during the fermentation, and thus it is necessary to cool the medium during the fermentation.

By the way, enzymes and proteins produced by thermophilic bacteria are generally stable at elevated temperatures, and also stable against pH variation or organic solvents. Therefore, applications thereof as diagnostic regents, industrial catalysts and so forth have been highly developed. If it becomes possible to produce L-lysine by fermentation at elevated temperatures by utilizing such stability and durability of enzymes derived from thermophilic bacteria, the cooling of the medium becomes unnecessary, and therefore the cost for cooling during the fermentation can be reduced. Moreover, if fermentation at elevated temperatures is realized, it is expected that the reaction rate may also be improved

SUMMARY OF THE INVENTION

The present invention is accomplished in view of the aforementioned technical aspect, and its object is to obtain genes of the L-lysine biosynthesis system of thermophilic bacteria and thereby provide novel methods for producing L-lysine.

The inventors of the present invention assiduously studied in order to achieve the aforementioned object. As a result, they successfully isolated genes that coded for DDPS and DDPR from *Bacillus methanolicus*, which is one of the thermophilic Bacillus bacteria, and determined the nucleotide sequences of these genes. Thus, they accomplished the present invention.

That is, the present invention provides the followings.

(1) A protein defined in the following (A) or (B):
  (A) a protein which has the amino acid sequence of SEQ ID NO: 2 shown in Sequence Listing, or (B) a protein which has an amino acid sequence of SEQ ID NO: 2 shown in Sequence Listing including substitution, deletion, insertion, addition or inversion of one or several amino acids, and has dihydrodipicolinate synthase activity.

(2) A DNA which codes for a protein defined in the following (A) or (B):
  (A) a protein which has the amino acid sequence of SEQ ID NO: 2 shown in Sequence Listing, or
  (B) a protein which has an amino acid sequence of SEQ ID NO: 2 shown in Sequence Listing including substitution, deletion, insertion, addition or inversion of one or several amino acids, and has dihydrodipicolinate synthase activity.

(3) The DNA according to (2), which is a DNA defined in the following (a) or (b):
  (a) a DNA which has a nucleotide sequence comprising at least the nucleotide sequence of the nucleotide numbers 1 to 924 in SEQ ID NO: 1 shown in Sequence Listing; or
  (b) a DNA which is hybridizable with a nucleotide sequence comprising at least the nucleotide sequence of the nucleotide numbers 1 to 924 in SEQ ID NO: 1 shown in Sequence Listing under a stringent condition, and codes for a protein having dihydrodipicolinate synthase activity.

(4) The DNA according to (3), wherein the stringent condition is a condition in which washing is performed at 60° C., 1×SSC and 0.1% SDS.

(5) A protein defined in the following (C) or (D):
  (C) a protein which has the amino acid sequence of SEQ ID NO: 4 shown in Sequence Listing, or
  (D) a protein which has an amino acid sequence of SEQ ID NO: 4 shown in Sequence Listing including substitution, deletion, insertion, addition or inversion of one or several amino acids, and has dihydrodipicolinate reductase activity.

(6) A DNA which codes for a protein defined in the following (C) or (D):
  (C) a protein which has the amino acid sequence of SEQ ID NO: 4 shown in Sequence Listing, or
  (D) a protein which has an amino acid sequence of SEQ ID NO: 4 shown in Sequence Listing including substitution, deletion, insertion, addition or inversion of one or several amino acids, and has dihydrodipicolinate reductase activity.
(7) The DNA according to (6), which is a DNA defined in the following (c) or (d):
  (c) a DNA which has a nucleotide sequence comprising at least the nucleotide sequence of the nucleotide numbers 1 to 798 in SEQ ID NO: 3 shown in Sequence Listing; or
  (d) a DNA which is hybridizable with a nucleotide sequence comprising at least the nucleotide sequence of the nucleotide numbers 1 to 798 in SEQ ID NO: 3 shown in Sequence Listing under a stringent condition, and codes for a protein having dihydrodipicolinate reductase activity.
(8) The DNA according to (7), wherein the stringent condition is a condition in which washing is performed at 60° C., 1×SSC and 0.1% SDS.
(9) A microorganism which is introduced with the DNA according to (2) or the DNA according to (6) or the both in a form that allows expression of a protein encoded by each DNA.
(10) A method for producing L-lysine, which comprises culturing the microorganism according to (9) in a medium to produce and accumulate L-lysine in the medium, and collecting the L-lysine from the medium.

In the present invention, the expression of "to have dihydrodipicolinate synthase activity" is used to mean to have an activity for catalyzing the reaction of dehydration condensation of aspartic acid semialdehyde and pyruvic acid to generate dihydrodipicolinate. The expression of "to have dihydrodipicolinate reductase activity" is used to mean to have an activity for catalyzing the reaction of reduction of dihydrodipicolinate to generate piperidinedicarboxylic acid, and to mean that the activity is higher at 50° C. than at 37° C.

According to the present invention, there are provided DDPS and DDPR, which are involved in the L-lysine biosynthesis, with excellent heat resistance, and genes coding for them.

PREFERRED EMBODIMENTS OF THE INVENTION

Hereafter, the present invention will be explained in detail.

The DNA of the present invention can be obtained through selection of clones containing a DDPS gene or a DDPR gene based on recovery of auxotrophy in mutant strains of microorganisms deficient in DDPS or DDPR used as an index from a gene library of thermophilic Bacillus bacteria, for example, *Bacillus methanolicus*.

The method for obtaining the DNA of the present invention will be explained below.

<1> Production of Gene Library of *Bacillus methanolicus*

A gene library of *Bacillus methanolicus* can be produced, for example, as follows. First, the total chromosome DNA is prepared by the method of Saito et al. (Saito, H. and Miura, K., *Biochem. Biophys. Acta,* 72, 619–629, (1963)) or the like from a wild-type strain of *Bacillus methanolicus,* for example, *Bacillus methanolicus* PB1 (NCIMB13113) strain, and partially digested with a suitable restriction enzyme, for example, Sau3AI and so forth to obtain a mixture of various fragments. If the degree of the digestion is controlled by adjusting digestion reaction time and so forth, restriction enzymes of a wide range can be used.

Subsequently, the digested chromosome DNA fragments are ligated to vector DNA autonomously replicable within *Escherichia coli* cells to produce recombinant DNA. More specifically, a restriction enzyme producing the same end nucleotide sequence as the restriction enzyme used for the digestion of the chromosome DNA is allowed to act on the vector DNA to fully digest the vector and cleave it. Then, the mixture of the chromosome DNA fragments and the cleaved vector DNA obtained as described above are mixed, and a DNA ligase, preferably T4 DNA ligase, is allowed to act on the mixture to obtain recombinant DNA.

By using the obtained recombinant DNA, *Escherichia coli,* for example, the *Escherichia coli* JM109 strain and so forth, is transformed, and a gene library solution can be prepared from culture of obtained transformants. The transformation can be performed by, for example, the method of D. M. Morrison (Methods in Enzymology, 68, 326 (1979)) and the method in which recipient cells are treated with calcium chloride so as to increase the permeability of the cells for DNA (Mandel, M. and Higa, A., J. Mol. Biol., 53, 159 (1970)). Electroporation was employed in the examples mentioned below.

Examples of the vector include, for example, pUC19, pUC18, pBR322, pHSG299, pHSG298, pHSG399, pHSG398, RSF100, pMW119, pMW118, pMW219, pMW218, pSTV28 and so forth. In addition, phage vectors can also be used. For example, since a chloramphenicol resistance gene is contained in pSTV28, only transformants harboring the vector or the recombinant DNA can be grown by using a medium containing chloramphenicol when that vector is used.

Examples of the method for collecting the recombinant DNA from the cells after the transformants are cultured include the alkali SDS method and so forth.

<2> Screening of Clones Containing DDPS Gene or DDPR Gene

By using a gene library solution of *Bacillus methanolicus* obtained as described above, a mutant strain of microorganism deficient in DDPS or DDPR is transformed, and clones showing recovery of auxotrophy are selected. Examples of such a mutant strain of microorganism deficient in DDPS include the *Escherichia coli* AT998 (CGSC4548) strain, which is deficient in DDPS. Since the *Escherichia coli* AT998 strain is deficient in the DDPS gene, it cannot grow in a minimal medium that does not contain diaminopimelate. On the other hand, a transformant strain thereof which harbors the DDPS gene derived from *Bacillus methanolicus* can grow in the minimal medium, because the gene functions. Therefore, a DNA fragment containing the DDPS gene can be obtained by selecting a transformant strain that can grow in the minimal medium and collecting recombinant DNA from the strain.

Examples of the mutant strain of microorganism deficient in DDPR include the *Escherichia coli* AT999 strain (CGSC 4549), which is deficient in the DDPR gene. Since the *Escherichia coil* AT999 strain is deficient in the DDPR gene, it shows only a slow growth rate even in a complete medium such as L medium if it does not contain diaminopimelate. On the other hand, a transformant strain thereof which harbors the DDPR gene derived from *Bacillus methanolicus* shows normal growth, because the gene functions. Further, the *Escherichia coli* AT999 cannot grow in a minimal medium, whereas a transformant strain thereof which harbors the DDPR gene derived from *Bacillus methanolicus* can grow in the minimal medium, because the gene functions. Therefore, a DNA fragment containing the DDPR gene can be obtained by selecting a transformant strain which can grow in the minimal medium and collecting recombinant DNA from the strain.

By extracting an inserted DNA fragment from the obtained recombinant DNA and determining nucleotide sequence of the fragment, the nucleotide sequence and the amino acid sequence of the DDPS gene or the DDPR gene and DDPS or DDPR can be determined.

Determination of nucleotide sequences, digestion and ligation of DNA and so forth may be attained by those methods commonly used for gene cloning (detailed in, for example, Sambrook J., Fritsch, E. F. and Maniatis, T., 1989, Molecular Cloning: A Laboratory Manual, Second edition, Cold Spring Harbor Laboratory Press, Cold Spring Harbor, N.Y. etc.). They can also be conducted according to instructions attached to reagents such as restriction enzymes and kits.

The DDPS gene of the present invention codes for DDPS that has the amino acid sequence of SEQ ID NO: 2 shown in Sequence Listing. Specific examples of the DDPS gene of the present invention include DNA that has the nucleotide sequence of SEQ ID NO: 1. Further, the DDPS gene of the present invention may have a nucleotide sequence including replacement of codons for each amino acid with equivalent codons, so long as the sequence codes for the same amino acid sequence as the amino acid sequence shown as SEQ ID NO: 2.

Further, the DDPS gene of the present invention may be one coding for a protein which has an amino acid sequence of SEQ ID NO: 2 including substitution, deletion, insertion, addition or inversion of one or several amino acids, or one coding for a protein which has DDPS activity. The term "several" amino acids used herein means preferably 1–50 amino acids, more preferably 1–10 amino acids. Homology between the DDPS gene of the present invention and a known DDPS gene of *Bacillus subtilis* (*B. subtilis*) is 65.9% on the basis of the nucleotide sequence, and 64.8% on the basis of the encoded amino acid sequence.

The DDPR gene of the present invention codes for DDPR that has the amino acid sequence of SEQ ID NO: 4 shown in Sequence Listing. Specific examples of the DDPR gene of the present invention include DNA that has the nucleotide sequence of SEQ ID NO: 3. Further, the DDPR gene of the present invention may have a nucleotide sequence including replacement of codons for each amino acid with equivalent codons, so long as the sequence codes for the same amino acid sequence as the amino acid sequence shown as SEQ ID NO: 4.

Further, the DDPR gene of the present invention may be one coding for a protein which has an amino acid sequence of SEQ ID NO: 4 including substitution, deletion, insertion, addition or inversion of one or several amino acids, or one coding for a protein which has DDPR activity. The term "several" amino acids used herein means preferably 1–40 amino acids, more preferably 1–10 amino acids. Homology between the DDPR gene of the present invention and a known DDPR gene of *Bacillus subtilis* (*B. subtilis*) is 66.7% on the basis of the nucleotide sequence, and 67.5% on the basis of the encoded amino acid sequence.

DNA that codes for the substantially same protein as DDPS or DDPR as described above is obtained by modifying the nucleotide sequence, for example, by means of the site-directed mutagenesis method so that one or more amino acid residues at a specific site should contain substitution, deletion, insertion, addition or inversion. DNA modified as described above may also be obtained by conventionally known mutation treatments. Such mutation treatments includes a method for treating DNA coding for DDPS or DDPR in vitro, for example, with hydroxylamine or the like, and a method for treating a microorganism, for example, a bacterium belonging to the genus Escherichia, harboring DNA coding for DDPS or DDPR with ultraviolet irradiation or a mutagenizing agent usually used for the mutation treatment such as N-methyl-N'-nitro-N-nitrosoguanidine (NTG) and nitrous acid.

The substitution, deletion, insertion, addition, or inversion of nucleotides as described above also includes mutation (mutant or variant) which naturally occurs, for example, due to the individual difference or the difference in species or genus of the microorganism that harbors DDPS or DDPR.

Such DNA coding for substantially the same protein as DDPS or DDPR is obtained by expressing DNA having mutation described above in an appropriate cell, and investigating the DDPS or DDPR activity of the expression product. DNA coding for substantially the same protein as DDPS or DDPR is also obtained by isolating DNA which is hybridizable with a nucleotide sequence comprising the nucleotide sequence of SEQ ID NO: 1 or 3 shown in Sequence Listing or a part thereof, for example, a probe which can be prepared from the nucleotide sequence of SEQ ID NO: 1 or 3 by PCR, under a stringent condition, and codes for a protein having DDPS or DDPR activity.

The "stringent condition" referred to herein is a condition under which a so-called specific hybrid is formed, and a non-specific hybrid is not formed. It is difficult to clearly define this condition by using numerical values. However, for example, the stringent condition includes a condition under which DNA's having high homology, for example, DNA's having homology of not less than 40% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS (see, for example, Sambrook, J., Fritsch, E. F. and Maniatis, T., Molecular Cloning: A Laboratory Manual, Second edition, 1989, Cold Spring Harbor Laboratory Press, Cold Spring Harbor, N.Y. etc.).

Such genes, which are hybridizable under the condition as described above, includes those having a stop codon generated in a coding region of the genes, and those having no activity due to mutation of active center. However, such mutants can be easily removed by ligating the genes with a commercially available activity expression vector, and measuring the DDPS or DDPR activity. The DDPS activity can be measured by, for example, the method of Yugari et al. (Yugari Y. and Gilvarg C., *Journal of Biological Chemistry*, 240, 4710 (1962)). Specifically, for example, the DDPS activity can be measured by allowing a reaction of 100 μl of 500 mM imidazole hydrochloride (pH 7.5), 100 μl of 20 mM aspartic acid semialdehyde (which can be synthesized by the method described in Black S. and Write N., *Journal of Biological Chemistry*, 213, 51 (1955)), 100 μl of 20 mM sodium pyruvate and 100 μl of an enzyme solution in a total volume of 1 ml and measuring increase of absorbance at 270 nm.

The DDPR activity can be measured by, for example, the method of Tamir et al. (Tamir H. and Gilvarg C., *Journal of*

*Biological Chemistry*, 249, 3034 (1974)). Specifically, for example, the DDPR activity can be measured by allowing a reaction of 100 μl of 500 mM imidazole hydrochloride (pH 7.5), 100 μl of dihydrodipicolinic acid, 100 μl of NADPH and 100 μl of an enzyme solution in a total volume of 1 ml and measuring decrease of absorbance at 340 nm.

Because the nucleotide sequences of the genes which code for DDPS and DDPR derived from *Bacillus methanolicus* were elucidated by the present invention, the DNA sequence which codes for DDPS or DDPR can be obtained from *Bacillus methanolicus* gene library by hybridization using an oligonucleotide probe prepared based on each of the sequences. DNA sequences which code for the enzymes can also be obtained by amplification from *Bacillus methanolicus* chromosome DNA by PCR (polymerase chain reaction) using oligonucleotide primers prepared based on the aforementioned nucleotide sequences.

<3> Application of DDPS Gene and DDPR Gene

The DDPS gene and the DDPR gene of the present invention can be used for production of DDPS and DDPR. That is, DDPS can be produced by introducing DNA containing the DDPS gene into a suitable host cell, and culturing the obtained transformant to allow expression of the DNA. DDPR can be produced by introducing DNA containing the DDPR gene into a suitable host cell, and culturing the obtained transformant to allow expression of the DNA. The produced DDPS protein or DDPR protein can be collected from the culture and purified by techniques used for usual purification of proteins such as salting out, solvent precipitation, gel filtration chromatography and ion exchange chromatography.

The DDPS gene and the DDPR gene can also be utilized for breeding of L-lysine producing bacteria. By introducing the DDPS gene, the DDPR gene or the both into a microorganism, L-lysine biosynthesis is enhanced and thus L-lysine producing ability is improved.

Examples of the host cell into which the DDPS gene or the DDPR gene is introduced include Escherichia bacteria such as *Escherichia coli*, coryneform bacteria such as *Brevibacterium lactofermentum*, Bacillus bacteria such as *Bacillus methanolicus* and so forth. Examples of the vector used for introducing the DDPS gene or the DDPR gene into these hosts include, as for Escherichia bacteria, those mentioned above. As for coryneform bacteria, the following vectors can be mentioned. There are indicated microorganisms which harbors each vector, and accession numbers thereof at international depositories are shown in the parentheses, respectively.

pAJ655
 *Escherichia coli* AJ11882 (FERM BP-136)
 *Corynebacterium glutamicum* SR8201
(ATCC39135)
pAJ1844
 *Escherichia coli* AJ11883(FERM BP-137)
 *Corynebacterium glutamicum* SR8202
(ATCC39136)
 pAJ611 *Escherichia coli* AJ11884 (FERM BP-138)
 pAJ3148 *Corynebacterium glutamicum* SR8203
(ATCC39137)
 pAJ440 *Bacillus subtilis* AJ11901 (FERM BP-140)

These vectors are obtained from deposited microorganisms as follows. Cells collected at the logarithmic growth phase are lysed with lysozyme and SDS to give a lysate, from which a supernatant solution is obtained by centrifugation at 30,000×g. Polyethylene glycol is added to the supernatant solution to perform fractional purification by means of cesium chloride-ethidium bromide equilibrium density gradient centrifugation.

In order to introduce a plasmid into *E. coli* to transform it, there may be used a method in which recipient cells are treated with calcium chloride so as to increase the permeability of the cells for DNA (Mandel, M. and Higa, A., *J. Mol. Biol.*, 53, 159 (1970)) and so forth.

Examples of the vector for Bacillus bacteria include, for example, pUB110, pHY300PLK, pHV1248, pE194, pC194, pBC16, pSA0501, pSA2100, pAM77, pT181, pBD6, pBD8, pBD64, pHV14 and so forth.

Transformation of coryneform bacteria may be performed by the electric pulse method (Sugimoto et al., Japanese Pat. Publication Laid-Open No. 2-207791/1990). Transformation of Bacillus bacteria may be performed by a method of making host sells into the protoplast or spheroplast followed by introducing recombinant DNA into the DNA-recipient cells (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci., USA*, 75, 1929 (1978)).

The DDPS gene or the DDPR gene to be introduced may be introduced into a host with a promoter proper to the gene, or the structural gene ligated to another promoter may be introduced. Examples of such a promoter include lac promoter, trp promoter, trc promoter, tac promoter, $P_R$ promoter and $P_L$ promoter of λ phage, tet promoter, amyE promoter, spac promoter and so forth.

L-lysine can be produced by culturing a microorganism introduced with the DDPS gene or the DDPR gene or the both genes and having L-lysine producing ability in a medium to produce and accumulate L-lysine in the medium, and collecting the L-lysine from the medium.

Although medium and culture conditions can suitably be selected according to kind of the host microorganism to be used, usual media can be used, which contain a nitrogen source, inorganic ions and other organic trace amount nutrients as required.

As the carbon source, there can be used saccharides such as glucose, lactose, galactose, fructose and hydrolysate of starch, alcohols such as glycerol and sorbitol, organic acids such as fumaric acid, citric acid and succinic acid and so forth.

When a methanol assimilating bacterium such as *Bacillus methanolicus* is used as the microorganism of the present invention, methanol can be preferably used as the carbon source.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the inorganic ions or sources thereof, a small amount of potassium phosphate, magnesium sulfate, iron ions, manganese ions and so forth may be added. As a trace amount organic nutrient, it is desirable to add a suitable amount of required substances such as L-homoserine and vitamin $B_1$, yeast extract and so forth as required.

The culture is performed under conditions suitable for growth of a microorganism to be used. In general, it is preferably performed for 16 to 72 hours under an aerobic condition, and the culture temperature is controlled to be 20 to 45° C., and pH to be 5–8.5 during the culture. For adjusting pH, inorganic or organic acidic or alkaline substances, ammonia gas and so forth can be used. Further, when a thermophilic bacterium is used as a host, it can be cultured at a culture temperature of 42 to 60° C.

Collection of L-lysine from the culture can usually be carried out by using a combination of known techniques such as techniques using ion exchange resins, precipitation methods and so forth.

EXAMPLES

Hereafter, the present invention will be further specifically explained with reference to the following examples.

The reagents used were obtained from Wako Pure Chemicals or Nakarai Tesque unless otherwise indicated. The compositions of the media used in each example are shown below. All the media were subjected to steam sterilization at 120° C. for 20 minutes after the components were dissolved.

| [L medium] | |
|---|---|
| Bacto trypton (DIFCO) | 1% |
| Yeast extract (DIFCO) | 0.5% |
| NaCl | 0.5% |
| [L agar medium] | |
| L medium | |
| Bacto aqar (DIFCO) | 1.5% |
| [SOC medium] | |
| Bacto trypton (DIFCO) | 2% |
| Yeast extract (DIFCO) | 0.5% |
| NaCl | 10 mM |
| KCl | 2.5 mM |
| $MgSO_4$ | 10 mM |
| $MgCl_2$ | 10 mM |
| Glucose | 20 mM |

[The components except for magnesium solution and glucose were steam-sterilized, then added with 2 M magnesium stock solution (1 M $MgSO_4$, 1 M $MgCl_2$) and 2 M glucose solution, which solutions had been passed through a 0.22 μm filter beforehand, and passed through a 0.22 μm filter again.]

| [TS medium] | |
|---|---|
| Bacto trypton (DIFCO) | 1.5% |
| Bactosoyton (DIFCO) | 0.5% |
| NaCl | 0.5% |
| [TS agar medium] | |
| TS medium | |
| Bacto agar (DIFCO) | 1.5% |
| [M9 minimal medium] | |
| $Na_2HPO_4 \cdot 12H_2O$ | 8% |
| $KH_2PO_4$ | 1.5% |
| NaCl | 2.5% |
| $NH_4Cl$ | 0.5% |
| $MgSO_4 \cdot 7H_2O$ | 246.48 mg/L |
| Glucose | 0.5% |
| pH 7.0 | |

[$MgSO_4$ and glucose were separately sterilized and added. A suitable amount of amino acids and vitamins were added as required.]

| [M9 minimal agar medium] | |
|---|---|
| M9 minimal medium | |
| Bacto aqar (PIFCO) | 1.5% |

Example 1

Cloning of DDPS Gene of *Bacillus methanolicus* PB1 Strain (1) Preparation of Chromosome DNA from *Bacillus methanolicus*

One loop of the *Bacillus methanolicus* PB1 strain (NCIMB13113) was inoculated into 5 ml of TS medium contained in a test tube, and cultured overnight at 50° C. with shaking. The obtained culture was inoculated into 50 ml of TS medium contained in a 500-ml volume Sakaguchi flask at a concentration of 1%, and cultured at 50° C. for 5–6 hours, and the cells were collected by centrifugation. The cells were suspended in 50 ml of TEN solution [solution comprising 50 mM Tris-HCl (pH 8.0), 10 mM EDTA, 20 mM NaCl (pH 8.0)], collected by centrifugation, and suspended again in 5 ml of TEN solution containing 5 mg/ml of lysozyme and 10 μg/ml of ribonuclease A.

The suspension was maintained at 37° C. for 30 minutes, and then added with proteinase K and sodium laurylsulfate at final concentrations of 10 μg/ml and 0.5%, respectively. The suspension was maintained at 70° C. for 2 hours, then added with an equal volume of a saturated phenol solution (phenol solution saturated with 10 mM Tris-HCl (pH 8.0)), and centrifuged. The supernatant was collected, added and mixed with an equal volume of a phenol/chloroform solution (phenol:chloroform:isoamyl alcohol=25:24:1), and centrifuged.

The supernatant was collected, and the same procedure as above was repeated by adding an equal volume of a chloroform solution (chloroform:isoamyl alcohol=24:1). The supernatant was added with 1/10 volume of 3 M sodium acetate (pH 4.8) and 2.5-fold volume of ethanol to precipitate chromosome DNA. The precipitate was collected by centrifugation, washed with 70% ethanol, dried under vacuum, and dissolved in an appropriate amount of TE solution (10 mM Tris-HCl, 1 mM EDTA (pH 8.0)).

(2) Ligation of Vector DNA and Chromosome DNA

50 μl of the chromosome DNA (1 μg/μl) obtained in the above (1), 20 μl of H buffer (500 mM Tris-HCl, 100 mM $MgCl_2$, 10 mM dithiothreitol, 1000 mM NaCl (pH 7.5)) and 8 units of restriction enzyme Sau3AI (Takara Shuzo) were allowed to react in a total volume of 200 μl at 37° C. for 10 minutes, and then the reaction mixture was mixed with 200 μl of the phenol/chloroform solution to stop the reaction.

The mixture was centrifuged to obtain an upper layer, which was separated on 0.8% agarose gel. A DNA fragment corresponding to 2–8 kilo base pairs (abbreviated as "kbp" hereinafter) was collected from the gel using EASYTRAP (glass powder for collection of DNA, produced by Takara Shuzo) to obtain 50 μl of a fractionated DNA solution.

Separately, 5 μl of 0.5 μg/μl plasmid pSTV28 (produced by Takara Shuzo), 2 μM of K buffer (200 mM Tris-HCl, 100 MM $MgCl_2$, 10 mM dithiothreitol, 1000 mM KCl (pH 8.5)) and 10 units of restriction enzyme BamHI (produced by Takara Shuzo) were allowed to react in a total volume of 20 μl at 37° C. for 2 hours, then added with 20 units of calf small intestine alkaline phosphatase (produced by Takara Shuzo), and further allowed to react for 30 minutes. The reaction mixture was added and mixed with an equal volume of the phenol/chloroform solution, and centrifuged. The supernatant was collected, and the same procedure as above was repeated by adding an equal volume of the chloroform solution. The supernatant was added with 1/10 volume of 3 M sodium acetate (pH 4.8) and 2.5-fold volume of ethanol to precipitate DNA. The precipitate was collected by centrifugation, washed with 70% ethanol, dried under vacuum, and dissolved in TE solution.

The Sau3AI digest of the chromosome DNA fractionated in the above (1) and the BamHI digest of pSTV28 were ligated by using Ligation Kit ver. 2 (Takara Shuzo). The ligation reaction mixture was added with 1/10 volume of 3 M sodium acetate (pH 4.8) and 2.5-fold volume of ethanol were added to precipitate DNA. The precipitate was collected by centrifugation, washed with 70% ethanol, dried under vacuum, and dissolved in TE solution.

(3) Preparation of Gene Library

One loop of Escherichia coli JM109 was inoculated into 5 ml of L medium contained in a test tube, and cultured overnight at 37° C. with shaking. The obtained culture was inoculated into 50 ml of L medium contained in a 500-ml volume Sakaguchi flask at a concentration of 1%, and cultured at 37° C. until $OD_{660}$ reached 0.5–0.6. The culture was cooled on ice for 15 minutes, and centrifuged at 4° C. to collect the cells. The cells were washed by suspending them in 50 ml of ice-cooled water and subjecting the suspension to centrifugation. This procedure was repeated once again, and the cells were washed by suspending them in 50 ml of 10% glycerol solution cooled with ice and subjecting the suspension to centrifugation. The cells were suspended in an equal volume of 10% glycerol solution, and divided into portions of 50 μl volume. To 50 μl of the cell, 1 μl of the ligation solution prepared above was added, and the mixture was transferred to a cuvette (for exclusive use in an electroporation apparatus of BioRad Co., width of 0.1 cm) cooled with ice beforehand. Conditions of the electroporation apparatus were set at 1.8 kV and 25 μF, and the pulse controller was set at 200 ohms. The cuvette was mounted on the apparatus and pulse was applied. After the application of the pulse, the mixture was immediately added with 0.5 ml of SOC medium, transferred to a sterilized test tube, and cultured at 37° C. for 1 hour with shaking. The culture was plated on L agar medium containing 20 μg/ml of chloramphenicol, and incubated overnight at 37° C.

The emerged colonies were collected by scraping, inoculated into 50 ml of L medium in a 500-ml volume Sakaguchi flask, and cultured at 37° C. for 2 hours with shaking. Plasmid DNA was extracted from the cultured cells by the alkali SDS method to obtain a gene library solution.

(4) Isolation of Clone with DDPS Gene

The Escherichia coil AT998 strain deficient in the DDPS gene (CGSC 4548) was transformed with the aforementioned gene library solution by electroporation as described above. After application of pulse, SOC medium was added to the transformation solution, and the cells were cultured at 37° C. with shaking. The culture was centrifuged, and the cells were washed by suspending them in 5 ml of sterilized water and centrifuging the suspension. This washing procedure was repeated once again, and the cells were suspended in 500 μl of sterilized water. The suspension was plated on M9 minimal agar medium containing 20 μg/ml of chloramphenicol, and incubated at 37° C. for 2–3 days. Because the Escherichia coil AT998 strain is deficient in the DDPS gene, it cannot grow on M9 minimal medium not containing diaminopimelic acid. However, a transformant strain thereof which contains the DDPS gene derived from Bacillus methanolicus can grow on M9 minimal medium because the gene functions.

The recombinant vector was extracted from the emerged colonies, and the inserted fragment was confirmed. A transformant with the vector pSTV28 could not grow on M9 minimal medium, whereas the Escherichia coli AT998 strain transformed with the above recombinant plasmid grew on M9 minimal medium. Thus, it was confirmed that the obtained insert contained the DDPS gene.

The Escherichia coli AT998 strain which harbors the plasmid containing the DDPS gene obtained as described above was designated as Escherichia coli AJ13633. The AJ13633 strain was deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 26, 1999 as an accession number of FERM P-17485, and transferred from the original deposit to international deposit based on Budapest Treaty on Jul. 14, 2000, and has been deposited as deposition number of FERM BP-7221.

(5) Determination of Nucleotide Sequence of DDPS Gene

Plasmid containing the DDPS gene was prepared from the Escherichia coli AJ13633 strain, and the nucleotide sequence of the DDPS gene derived from the Bacillus methanolicus PB1 strain was determined by the dideoxy method. The coding region of the determined nucleotide sequence of the DDPS gene was shown as SEQ ID NO: 1. The amino acid sequence encoded by the nucleotide sequence is shown as SEQ ID NO: 2. Nucleotide and amino acid sequence were analyzed with the Genetyx-Mac computer program (Software Development Co., Tokyo, Japan). The homology analysis was carried out according to the method developed by Lipman and Peason (Science, 227, 1435–1441, 1985). As a result of the homology search, since this amino acid sequence showed a high homology of 64.8% with respect to DDPS derived from Bacillus subtilis belonging to the genus Bacillus like Bacillus methanolicus, the obtained gene was identified to be the DDPS gene derived from Bacillus methanolicus.

Example 2

Cloning of DDPR Gene of Bacillus methanolicus PR1 Strain (1) Isolation of Clone with DDPR Gene The Escherichia coli AT999 strain deficient in the DDPR gene (CGSC4549) was transformed with a gene library solution prepared in the same manner as Example 1(3) by electroporation in the same manner as described above. After pulse was applied, SOC medium was added to the transformation solution, and the cells were cultured at 37° C. with shaking. Then, the culture was plated on L agar medium containing 20 μg/ml of chloramphenicol, and incubated at 37° C. overnight. Since the Escherichia coli AT999 strain is deficient in the DDPR gene, it shows very slow growth in L medium that does not contain diaminopimelic acid. However, a transformant strain that contains the DDPR gene derived from Bacillus methanolicus shows normal growth even on L medium, since the gene functions. Further, the AT999 strain cannot grow on M9 minimal medium, whereas a transformant strain thereof that contains the DDPR gene derived from Bacillus methanolicus can grow on M9 minimal medium, since the gene functions.

A colony normally grown on L medium was cultured on M9 agar medium as streak culture to confirm that the DDPR gene was functioning in the transformant strain. Plasmid was extracted from colonies emerged on M9 medium, and an insert was confirmed. A transformant with the vector pSTV28 could not grow on M9 minimal medium, whereas the Escherichia coli AT998 strain transformed with the above recombinant plasmid grew on M9 minimal medium. Thus, it was confirmed that the obtained insert contained the DDPR gene.

The Escherichia coli AT999 strain which harbors the plasmid containing the DDPR gene obtained as described above was designated as Escherichia coli AJ13634. The AJ13634 strain was deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 26, 1999 as an accession number of FERM P-17486, and transferred from the original deposit to international deposit based on Budapest Treaty on Jul. 14, 2000, and has been deposited as deposition number of FERM BP-7222.

(2) Determination of Nucleotide Sequence of DDPR Gene

Plasmid containing the DDPR gene was prepared from the Escherichia coil AJ13634 strain, and the nucleotide sequence of the DDPR gene derived from the Bacillus methanolicus PB1 strain was determined by the dideoxy method. The coding region of the determined nucleotide sequence of the DDPS gene was shown as SEQ ID NO: 3. The amino acid sequence encoded by the nucleotide sequence is shown as SEQ ID NO: 4. Nucleotide and amino acid sequence were analyzed with the Genetyx-Mac computer program (Software Development Co., Tokyo, Japan). The homology analysis was carried out according to the method developed by Lipman and Peason (*Science*, 227, 1435–1441, 1985). As a result of the homology search, since this amino acid sequence showed a high homology of 67.5% with respect to DDPR derived from *Bacillus subtilis* belonging to the genus Bacillus like *Bacillus methanolicus*, the obtained gene was identified to be the DDPR gene derived from *Bacillus methanolicus*.

What is claimed is:

1. An isolated protein comprising a substitution, deletion, insertion or addition of not more than 50 amino acids in SEQ ID NO:2, which has dihydrodipicolinate synthase activity.

2. The isolated protein of claim 1, comprising substitution, deletion, insertion or addition of not more than 10 amino acids in SEQ ID NO:2.

3. An isolated protein which is encoded by a DNA that hybridizes under stringent conditions to nucleotides 1 to 924 of SEQ ID NO:1, wherein said stringent conditions comprise washing in 1×SSC and 0.1% SDS at 60° C. wherein said protein has dihydrodipicolinate synthase activity.

4. An isolated protein comprising the amino acid sequence of SEQ ID NO:2.

* * * * *